(12) United States Patent  
Kelly et al.

(10) Patent No.: US 9,841,419 B2
(45) Date of Patent: Dec. 12, 2017

(54) SENSOR DEVICE AND A METHOD OF SAMPLING (71) Applicant: KONINKLIJKE PHILIPS N.V., Eindhoven (NL)

(72) Inventors: Declan Patrick Kelly, Shanghai (CN); Weimin Xiao, Shanghai (CN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 17 days.

(21) Appl. No.: 14/425,128

(22) PCT Filed: Sep. 4, 2013

(86) PCT No.: PCT/IB2013/058272
§ 371 (c)(1),
(2) Date: Mar. 6, 2015

(87) PCT Pub. No.: WO2014/037880
PCT Pub. Date: Mar. 13, 2014

(65) Prior Publication Data
US 2015/0233908 A1    Aug. 20, 2015

(30) Foreign Application Priority Data

Sep. 4, 2012  (WO) ................ PCT/CN2012/080969

(51) Int. Cl.
*G01N 33/543* (2006.01)
*G01N 1/28* (2006.01)
*G01N 33/02* (2006.01)

(52) U.S. Cl.
CPC ......... *G01N 33/54326* (2013.01); *G01N 1/28* (2013.01); *G01N 33/02* (2013.01); *G01N 33/54386* (2013.01)

(58) Field of Classification Search
None
See application file for complete search history.

(56) References Cited

U.S. PATENT DOCUMENTS 8,945,946 B2     2/2015  Ikeda
2006/0257945 A1  11/2006  Masters et al.
(Continued)

FOREIGN PATENT DOCUMENTS

CN    101046464 A    10/2007
CN    101213452 A     7/2008
(Continued)

*Primary Examiner* — Rebecca Martinez (57) ABSTRACT

A sample is added to a chamber (12) in which magnetic particles (P) are provided. The sample includes a target component (T) and the chamber (12) has a detection surface (122). A magnetic force is exerted on the magnetic particles (P) to attract the magnetic particles (P) to the detection surface (122). The bound magnetic particles that captured the target component (T) in the magnetic particles (P) and the unbound magnetic particles that captured no target component (T) in the magnetic particles (P) are held at the detection surface (122). At least part of the sample is drained out of the chamber (12) and a new sample added to the chamber (12). The magnetic force exerted on the magnetic particles (P) is altered to release the unbound magnetic particles from the detection surface (122). An amount of the bound magnetic particles that are held at the detection surface (122) are measured. The target component (T) is preconcentrated by repeating the steps of magnetically binding the target component (T) from the newly added sample and washing the detection surface (122) from unbound magnetic particles.

12 Claims, 4 Drawing Sheets

(56) References Cited

U.S. PATENT DOCUMENTS

| | | |
|---|---|---|
| 2006/0286685 A1 | 12/2006 | Fitch et al. |
| 2008/0160639 A1 | 7/2008 | Su et al. |
| 2008/0206892 A1 | 8/2008 | Prins |
| 2009/0117670 A1 | 5/2009 | Van Der Wijk et al. |
| 2009/0170212 A1 | 7/2009 | Van Der Wijk et al. |
| 2010/0291712 A1 | 11/2010 | Vogeser |
| 2011/0207229 A1 | 8/2011 | Evers et al. |
| 2011/0244596 A1 | 10/2011 | Evers et al. |
| 2012/0164644 A1 | 6/2012 | Neely et al. |

FOREIGN PATENT DOCUMENTS

| | | |
|---|---|---|
| CN | 101438163 A | 5/2009 |
| JP | 2008541052 A | 11/2008 |
| JP | 2009545739 A | 12/2009 |
| WO | 2007030155 A | 3/2007 |
| WO | 2007129275 A2 | 11/2007 |
| WO | 2008015645 A2 | 2/2008 |
| WO | 2010134005 A1 | 11/2010 |
| WO | 2011027146 A2 | 3/2011 |
| WO | 2012035462 A1 | 3/2012 |

SENSOR DEVICE AND A METHOD OF SAMPLING

CROSS-REFERENCE TO PRIOR APPLICATIONS

This application is the U.S. National Phase application under 35 U.S.C. §371 of International Application No. PCT/IB2013/058272, filed on Sep. 4, 2013, which claims the benefit of Chinese Patent Application No. PCT/CN2012/080969, filed on Sep. 4, 2012. These applications are hereby incorporated by reference herein.

FIELD OF THE INVENTION

The present invention relates to a sensor device. Moreover, the present invention relates to a method of sampling.

BACKGROUND OF THE INVENTION

A biosensor is an analytical device for the detection of an analyte that combines a biological component with a physicochemical detector. The biosensor is now being developed for a variety of applications, such as healthcare, food safety, etc.

One of the current biosensors, for example Magnotech platform, works as follows. When a sample is poured into a chamber, the magnetic beads in the chamber begin to capture the target molecules in the sample via antibodies (called 'Target capture'). Then, a first magnetic field is applied to attract all of the magnetic beads to a detection surface, coated with antibodies, of the chamber (called 'Magnetic attraction'), wherein magnetic beads capturing the target molecules (i.e., bound magnetic beads) are bound to the detection surface via antigen-antibody reaction, and magnetic beads capturing no target molecule (i.e., unbound magnetic beads) are held at the detection surface via magnetic force. Next, a second magnetic field is applied to pull the unbound magnetic beads away from the detection surface (called 'Magnetic wash'). An optical method is then used to measure the amount of the bound magnetic beads at the detection surface and thereby the concentration of the target molecules in the sample.

The current biosensor can work with very small sample size, for example 100 µl, and have certain sensitivity for this sample size. However, this small sample size could be the limitation/disadvantage for applications such as food safety. First, the property of food sample determines that the sample size of 100 µl is less representative. Second, the sensitivity requirement in food safety is very high. Thus the small sample size may result in either false negative or longer enrichment time.

OBJECT AND SUMMARY OF THE INVENTION

Based on above concerns, in one aspect, one embodiment of the invention provides a sensor device. The sensor device comprises:
a chamber in which magnetic particles are provided, the chamber having a detection surface and configured to receive a sample in which a target component is included;
a magnetic manipulator configured to exert a magnetic force on the magnetic particles to attract the magnetic particles to the detection surface, wherein bound magnetic particles that capture the target component in the magnetic particles are held at the detection surface, and unbound magnetic particles that capture no target component in the magnetic particles are held at the detection surface as well; then to alter the magnetic force exerted on the magnetic particles to release the unbound magnetic particles from the detection surface;
a sample replacing unit configured to replace at least part of the sample in the chamber with a new sample;
a sensor unit configured to measure the amount of the bound magnetic particles that are held at the detection surface;
a control unit coupled to the magnetic manipulator, the sample replacing unit and the sensor unit, wherein the control unit is configured to perform the following operations repeatedly until a given cycles is reached,
control the magnetic manipulator to exert the magnetic force on the magnetic particles to attract the magnetic particles to the detection surface,
control the sample replacing unit to replace at least part of the sample in the chamber with the new sample,
control the magnetic manipulator to alter the magnetic force exerted on the magnetic particles to release the unbound magnetic particles from the detection surface;
and further configured to control the sensor unit to measure the amount of the bound magnetic particles that are bound to the detection surface when the given cycles is reached.

In this embodiment, the number of sample replacements (i.e. the given cycles) is predetermined and stored in the controller. During the operation of the sensor device, the controller will control the sample replacing unit to replace the sample in the chamber with a new sample until the given cycles is reached. As the sample in the chamber is replaced with a new sample by multiple times, the total sample volume for detection is increased and thus the sensitivity of the sensor device is improved.

Another embodiment of the invention provides a sensor device. The sensor device comprises:
a chamber in which magnetic particles are provided, the chamber having a detection surface and configured to receive a sample in which a target component is included;
a magnetic manipulator configured to exert a magnetic force on the magnetic particles to attract the magnetic particles to the detection surface, wherein bound magnetic particles that capture the target component in the magnetic particles are held at the detection surface, and unbound magnetic particles that capture no target component in the magnetic particles are held at the detection surface as well; and then to alter the magnetic force exerted on the magnetic particles to release the unbound magnetic particles from the detection surface;
a sample replacing unit configured to replace at least part of the sample in the chamber with a new sample;
a sensor unit configured to measure the amount of the bound magnetic particles that are held at the detection surface;
a control unit coupled to the magnetic manipulator, the sample replacing unit and the sensor unit and configured to perform the following operations;
i. control the magnetic manipulator to exert the magnetic force on the magnetic particles to attract the magnetic particles to the detection surface;
ii. control the magnetic manipulator to alter the magnetic force exerted on the magnetic particles to release the unbound magnetic particles from the detection surface;

iii. determine whether the amount of the bound magnetic particles that are held at the detection surface is above a predetermined threshold;
if no, the control unit is further configured to perform the following operation,
control the magnetic manipulator to exert the magnetic force on the magnetic particles to attract the magnetic particles to the detection surface;
control the sample replacing unit to replace at least part of the sample in the chamber with the new sample;
control the magnetic manipulator to alter the magnetic force exerted on the magnetic particles to release the unbound magnetic particles from the detection surface;
and then to perform the operation of i to iii.

In this embodiment, the number of sample replacements is determined based on the comparison of the measured amount of the bound magnetic particles and the predetermined threshold during the operation of the sensor device. Once the measured amount of the bound magnetic particles reaches the predetermined threshold, the sample replacing is ceased, which makes the detection of the sensor device more flexible.

In another aspect, one embodiment of the invention provides a method of sampling. The method comprises the steps of:

a. adding a sample to a chamber in which magnetic particles are provided, the sample including a target component and the chamber having a detection surface;

b. exerting a magnetic force on the magnetic particles to attract the magnetic particles to the detection surface, wherein bound magnetic particles that capture the target component in the magnetic particles are held at the detection surface, and unbound magnetic particles that capture no target component in the magnetic particles are held at the detection surface as well;

c. draining at least part of the sample out of the chamber and then adding a new sample to the chamber;

d. altering the magnetic force exerted on the magnetic particles to release the unbound magnetic particles from the detection surface;

e. repeating the steps b to d for a given cycles.

Another embodiment of the invention provides a method of sampling. The method comprises the steps of:

A. adding a sample to a chamber in which magnet particles are provided, the sample including a target component and the chamber having a detection surface;

B. exerting a magnetic force on the magnetic particles to attract the magnetic particles to the detection surface, wherein bound magnetic particles that capture the target component in the magnetic particles are held at the detection surface, and unbound magnetic particles that capture no target component in the magnetic particles are held at the detection surface as well;

C. altering the magnetic force exerted on the magnetic particles to release the unbound magnetic particles from the detection surface;

D. measuring the amount of the bound magnetic particles that are held at the detection surface;

E. determining whether the amount of the bound magnetic particles that are held at the detection surface is above a predetermined threshold;
if no, performing the following steps of:
exerting the magnetic force on the magnetic particles to attract the magnetic particles to the detection surface;
draining at least part of the sample out of the chamber and adding a new sample To the chamber;
altering the magnetic force exerted on the magnetic particles to release the unbound magnetic particles from the detection surface
going back to perform the steps B to E.

BRIEF DESCRIPTION OF THE DRAWINGS

The above and other objects and features of the present invention will become more apparent from the following detailed description considered in connection with the accompanying drawings, in which.

Throughout the above drawings, like reference numerals will be understood to refer to like, similar or corresponding features or functions.

DETAILED DESCRIPTION

Reference will now be made to embodiments of the invention, one or more examples of which are illustrated in the figures. The embodiments are provided by way of explanation of the invention, and are not meant as a limitation of the invention. For example, features illustrated or described as part of one embodiment may be used with another embodiment to yield still a further embodiment. It is intended that the invention encompass these and other modifications and variations as come within the scope and spirit of the invention.

The sensor device of the invention is applicable to a variety of detection scenarios, for example, the sensor device of the invention can be used to detect the concentration of target component in a sample.

The magnetic separation technology is applied in the sensor device of the invention to achieve the purpose of detection. In one example, the magnetic separation technology can be immunomagnetic separation which uses the mechanism of immune system.

Figure 1:
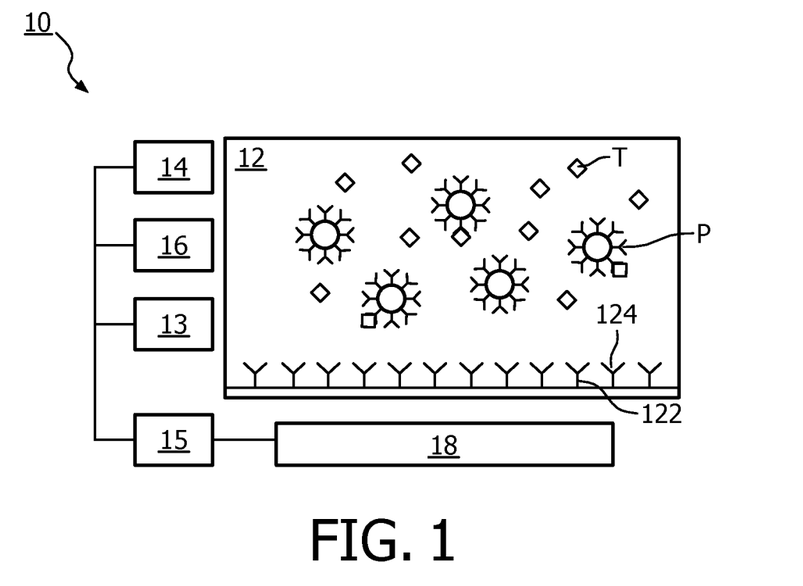
FIG. 1 shows a block diagram of a sensor device according to one embodiment of the invention.

FIG. 1 shows an exemplary sensor device 10 according to one embodiment of the invention. Referring to FIG. 1, the sensor device 10 comprises a chamber 12 for receiving a sample that includes a target component (e.g., antigens, for immunomagnetic separation). The chamber 12 may be an empty cavity, for example. Advantageously, the chamber 12 is made of a material that is substantially impervious to the sample. In the chamber 12, a bunch of magnetic particles P are provided. The magnetic particle may for example be magnetized or magnetizable bead, which is capable of capturing the target component T in the sample.

The chamber 12 has a detection surface 122 that carries binding sites 124 (e.g., antibodies) to which those magnetic particles that capture the target component (e.g., antigens)

can specifically bind to via antigen-antibody reaction. It shall be appreciated that there are also magnetic particles in the chamber 12 that cannot bind to the detection surface 122 because they did not capture the target component. The detection surface 122 may be the surface of a substrate, for example a silicon substrate in which microelectronic circuits are embedded, or a glass substrate in the case of optical measurement.

Figure 3:
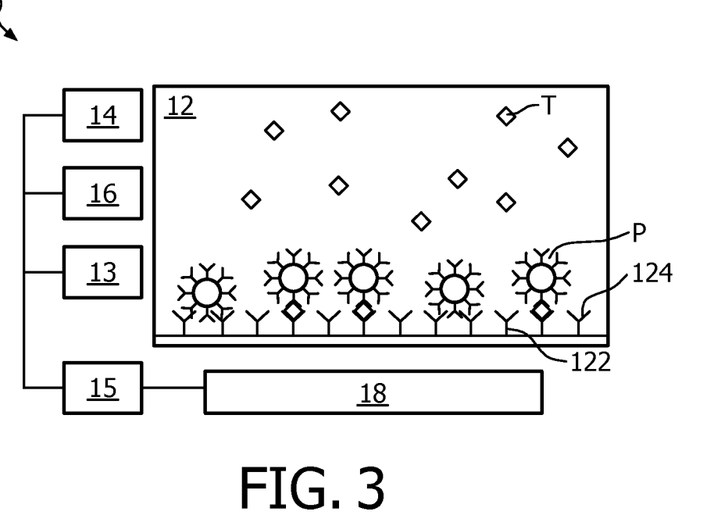
FIG. 3 shows a schematic view of magnetic attraction of the sensor device according to one embodiment of the invention.
Figure 4:
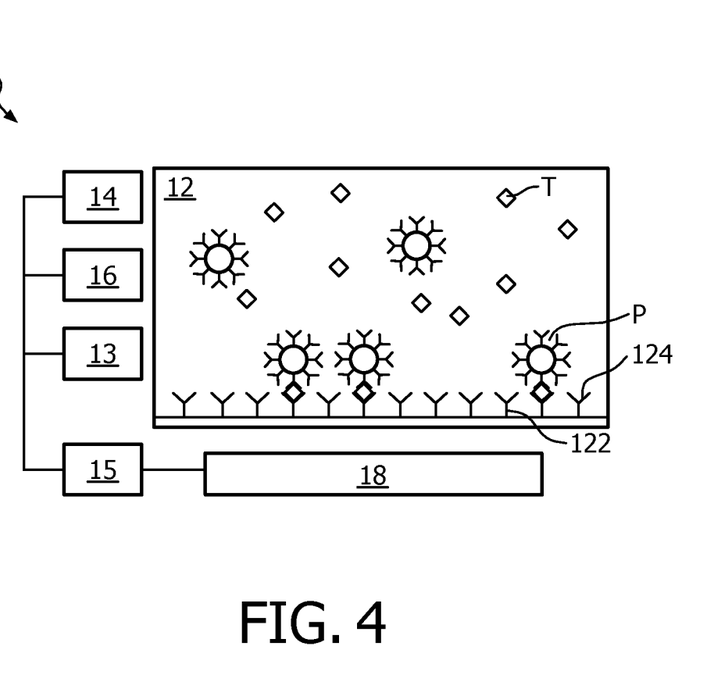
FIG. 4 shows a schematic view of magnetic wash of the sensor device according to one embodiment of the invention.

Still referring to FIG. 1, the sensor device 10 further comprises a magnetic manipulator 14 configured to exert a magnetic force on all of the magnetic particles in the chamber 12 so as to attract these magnetic particles to the detection surface 122 (called 'Magnetic attraction'). In all these magnetic particles, the magnetic particles that capture the target component (hereinafter referred to as 'bound magnetic particles') are held at the detection surface 122, for example via antigen-antibody reaction; and the remaining magnetic particles that do not capture the target component (hereinafter referred to as 'unbound magnetic particles') are held at the detection surface via magnetic force, as shown in FIG. 3. Moreover, the magnetic manipulator 14 is further configured to alter the magnetic force exerted on all of the magnetic particles so as to release the unbound magnetic particles from the detection surface 122 (called 'Magnetic wash'), as shown in FIG. 4.

Figure 2:
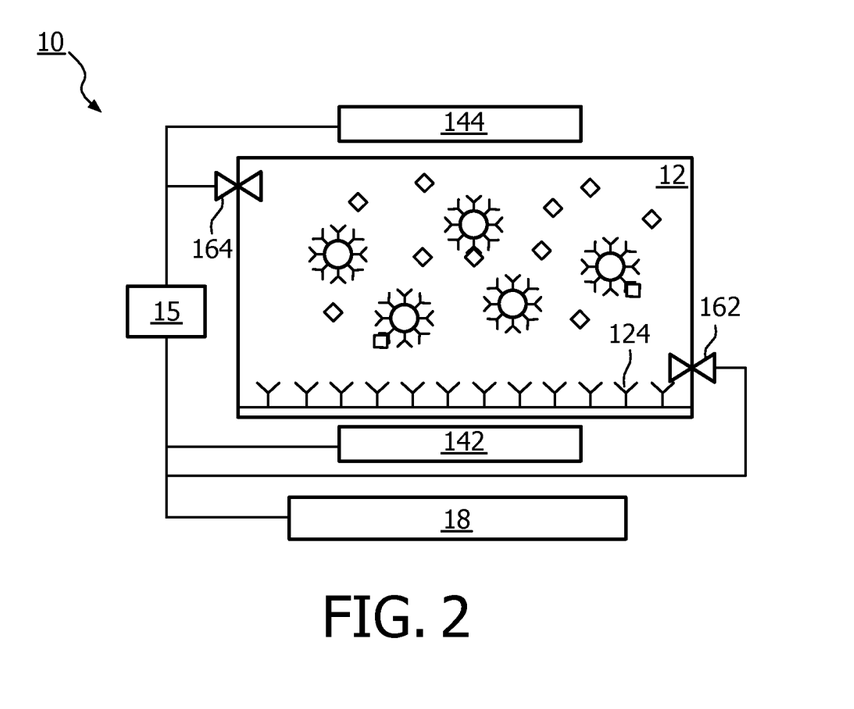
FIG. 2 shows an exemplary sensor device according to one embodiment of the invention.

The magnetic manipulator 14 can be achieved by a variety of ways. In one example, the magnetic manipulator 14 may include a first magnet 142 disposed below the chamber 12 and adjacent to the detection surface 122 and a second magnet 144 disposed above the chamber 12, as shown in FIG. 2. When the first magnet 142 is activated (i.e., switched on), a first magnetic field is generated so as to attract all of the magnetic particles to the detection surface 122, and then when the first magnet 142 is deactivated (i.e., switched off) and the second magnet 144 is activated, a second magnetic field that is opposite to the first magnetic field is generated so as to pull the unbound magnetic particles away from the detection surface 122. It is to be noted that the pulling force of the second magnetic field should be controlled to be smaller than the binding force of the bound magnetic particles at the detection surface 122 such that the bound magnetic particles can be retained on the detection surface 122 while the unbound magnetic particles are pulled away from the detection surface 122.

In another example, the magnetic manipulator 14 may only include the first magnet 142. When the first magnet 142 is activated, the first magnetic field is generated so as to attract all of the magnetic particles to the detection surface 122, and then when the first magnet 142 is deactivated, the first magnetic field is switched off and thereby the unbound magnetic particles are released from the detection surface 122.

Still referring to FIG. 1, the sensor device 10 further comprises a sample replacing unit 16 configured to replace at least part of the sample in the chamber 12 with a new sample that includes a target component.

The sample replacing unit 16 may take on various configurations, but generally includes an outflow valve 162 and an inflow valve 164 disposed at the chamber 12, as shown in FIG. 2. Advantageously, the outflow valve 162 is disposed at a lower position of the chamber 12, for example at the bottom of the chamber 12, such that at least part of the sample can be drained out of the chamber 12 by gravity when the outflow valve 162 is controlled to be open. Alternatively, a pump may also be used to pump at least part of the sample out of the chamber 12.

The inflow valve 164 may for example be in fluid communication with a container that contains plenty of new sample. When the outflow valve 162 is controlled to be closed and the inflow valve 164 is controlled to be open, the new sample in the container flows into the chamber 12.

Still referring to FIG. 1, the sensor device 10 further comprises a sensor unit 18 configured to measure the amount of the bound magnetic particles at the detection surface 122. Advantageously, the sensor unit 18 is disposed below the detection surface 122 of the chamber 12. The sensor unit 18 may be any suitable sensor to detect the presence of magnetic particles at the detection surface 122. For example, the sensor unit 18 may detect the presence of the bound magnetic particles via magnetic methods, optical methods, sonic methods, electrical methods, the combination thereof, etc.

Advantageously, the sensor device 10 may further comprise a mixing unit 13 configured to mix the magnetic particles and the target component when the sample/new sample is added into the chamber 12. In an example, the first magnet 142 and the second magnet 144 can be served as the mixing unit 13. To be specific, the first magnet 142 and the second magnet 144 are controlled to be switched on alternately to generate an alternate magnetic field, such that the good mixing of the magnetic particles and the target component can be achieved.

Still referring to FIG. 1, the sensor device 10 further comprise a controller 15 coupled to the magnetic manipulator 14, the mixing unit 13, the sample replacing unit 16 and the sensor unit 18, and configured to control the activities of these units. The controller 15 may be an MCU (Micro Control Unit), for example.

Based on different control strategies of the controller 15, the sensor device 10 can operate in different ways. Hereinafter, different operations of the sensor device 10 will be described respectively in connection with the configuration of the sensor device 10 described above and with reference to FIGS. 5 and 6.

Figure 5:
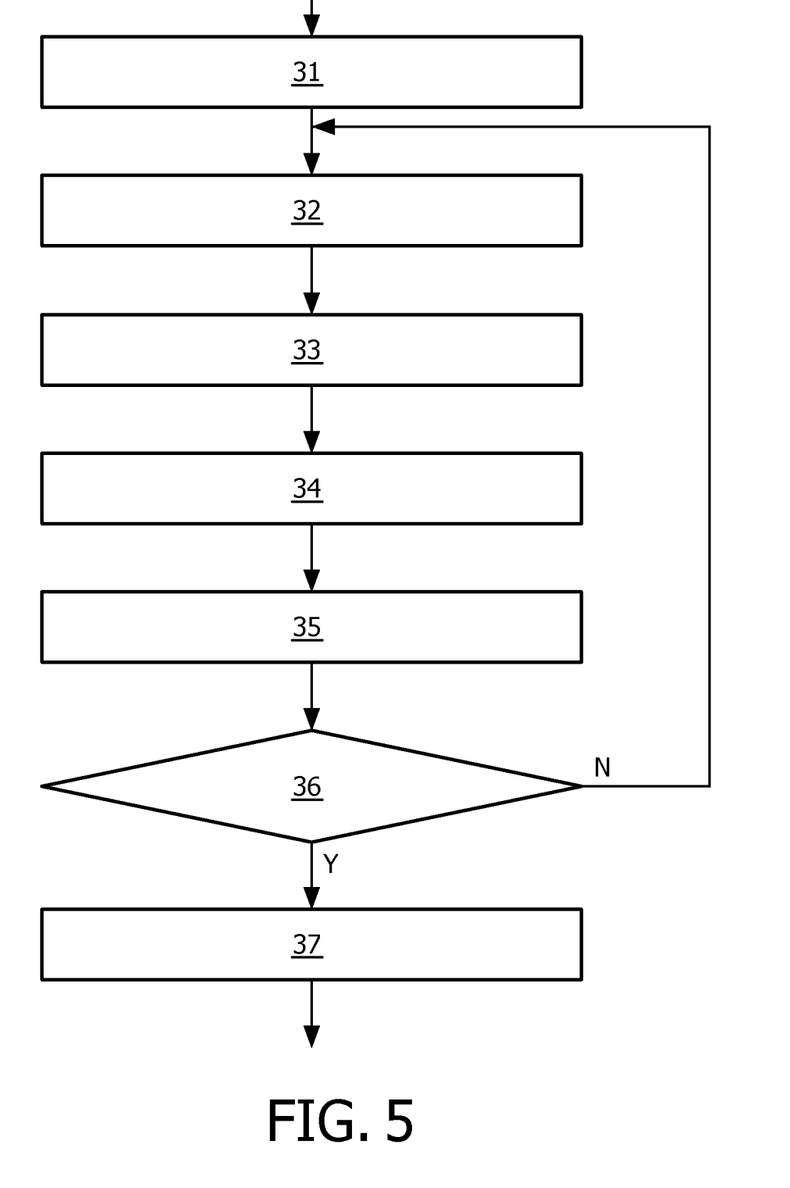
FIG. 5 shows a flow chart of a sampling and detection method implemented by the sensor device of FIG. 2.

In one embodiment, referring to FIG. 5, first, in Step 31, the sample is added to the chamber 12.

Then, in Step 32, the controller 15 controls the first magnet 142 and the second magnet 144 to be switched on alternately to generate an alternate magnetic field. Advantageously, the alternate magnetic field lasts for a predetermined duration, thus facilitating the good mixing of the magnetic particles and the target component in the sample. The predetermined duration may be preset according to the type of the sample, the amount of target component in the sample, etc. After the mixing, part of the magnetic particles capture the target component in the sample (i.e., bound magnetic particles), and the others do not capture the target component (i.e., unbound magnetic particles).

Next, in Step 33, the controller 15 controls the first magnet 142 to generate the first magnet field so as to attract all of the magnetic particles to the detection surface 122. For all of the magnetic particles that are attracted to the detection surface 122, the bound magnetic particles will be held at the detection surface 122, for example via antigen-antibody reaction; and the unbound magnetic particles will be held at the detection surface 122 via magnetic force.

Then, in Step 34, the controller 15 controls the outflow valve 162 to be open to drain at least part of the sample out of the chamber 12, and then controls the outflow valve 162 to be closed and the inflow valve 162 to be open to allow the new sample to flow into the chamber 12.

Further, in Step 35, the controller 15 controls the first magnet 142 to be switched off and the second magnet 144 to be switched on to generate the second magnetic field so as to pull the unbound magnetic particles away from the detection surface 122.

Next, in Step 36, the controller 15 determines whether a given cycles is reached. The given cycles may be preset according to the type of the sample, the sensitivity of the sensor unit 18, etc.

If the given cycles is not reached, the controller 15 continues to perform Steps 32 to 36. If the given cycles is reached, in Step 37, the controller 15 controls the sensor unit 18 to measure the amount of the bound magnetic particles at the detection surface 122. Based on the measured amount of the bound magnetic particles at the detection surface 122, the concentration of the target component in the sample can be obtained.

In this embodiment, the number of sample replacements (i.e., the given cycles) is predetermined and stored in the controller 15. During the operation of the sensor device 10, the controller 15 controls the sample replacing unit 16 to replace the sample in the chamber 12 with a new sample until the given cycles is reached. As the sample in the chamber 12 is replaced with a new sample by multiple times, the total sample volume for detection is increased and thus the sensitivity of sensor device 10 is improved.

Figure 6:
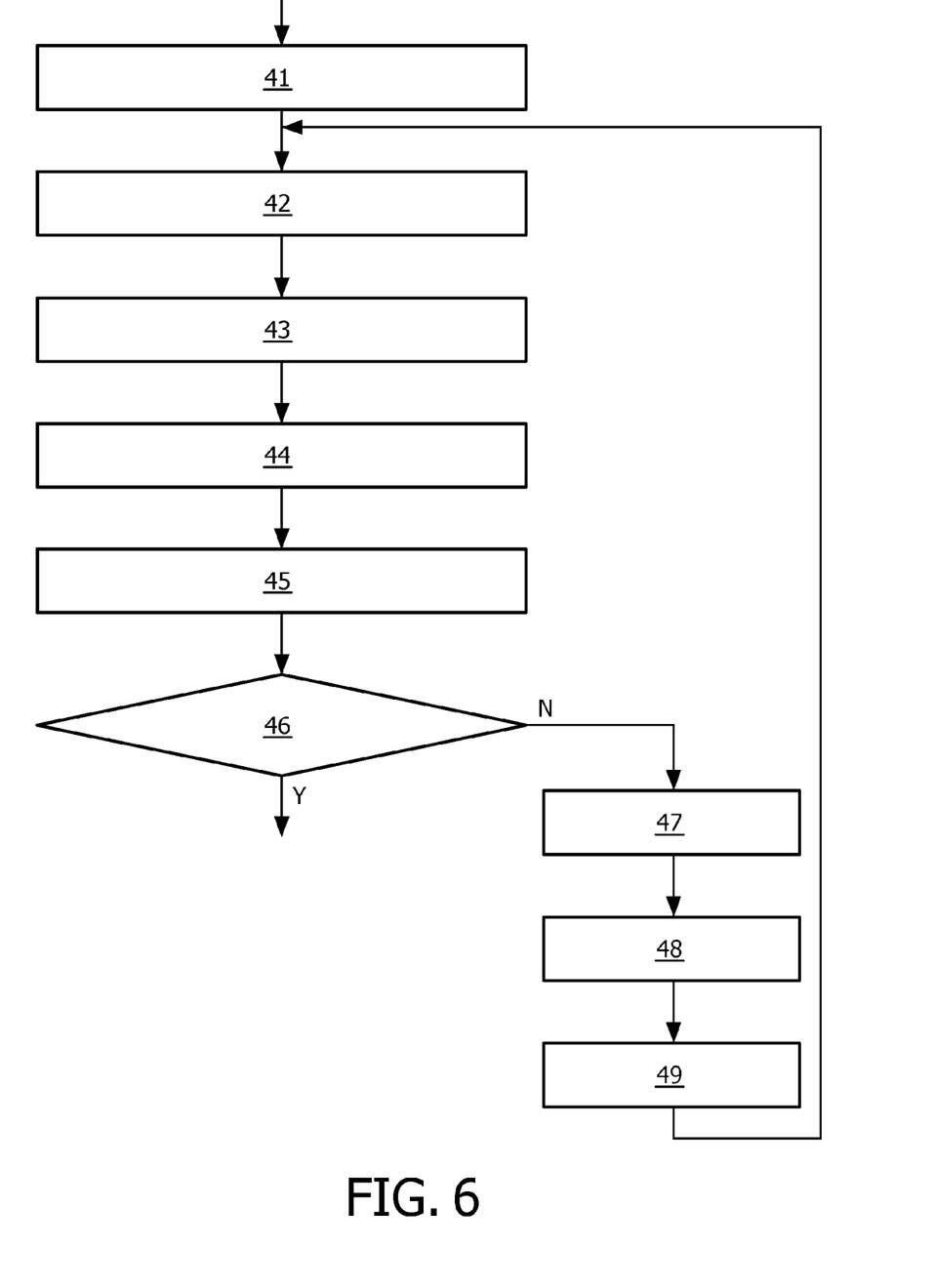
FIG. 6 shows a flow chart of another sampling and detection method implemented by the sensor device of FIG. 2.

In another embodiment, referring to FIG. 6, first, in Step 41, the sample is added to the chamber 12.

Then, in Step 42, the controller 15 controls the first magnet 142 and the second magnet 144 to be switched on alternately to generate an alternate magnetic field. Advantageously, the alternate magnetic field lasts for a predetermined duration, thus facilitating the good mixing of the magnetic particles and the target component in the sample. The predetermined duration may be preset according to the type of the sample, the amount of target component in the sample, etc. After the mixing, part of the magnetic particles capture the target component in the sample (i.e., bound magnetic particles), and the others do not capture the target component (i.e., unbound magnetic particles).

Next, in Step 43, the controller 15 controls the first magnet 142 to generate the first magnet field so as to attract all of the magnetic particles to the detection surface 122. For all of the magnetic particles that are attracted to the detection surface 122, the bound magnetic particles will be held at the detection surface 122, for example via antigen-antibody reaction; and the unbound magnetic particles will be held at the detection surface 122 via magnetic force.

Further, in Step 44, the controller 15 controls the first magnet 142 to be switched off and the second magnet 144 to be switched on to generate the second magnetic field so as to pull the unbound magnetic particles away from the detection surface 122.

Then, in Step 45, the controller 15 controls the sensor unit 18 to measure the amount of the bound magnetic particles at the detection surface 122.

Next, in Step 46, the controller 15 determines whether the amount of the bound magnetic particles at the detection surface 122 is above a predetermined threshold. The predetermined threshold may be determined based on the property of the sample and/or the sensor unit 18. For example, the predetermined threshold can be the quantification limit of the target component.

If the amount of the bound magnetic particles at the detection surface 122 is above the predetermined threshold, then this amount of the bound magnetic particles can be used to obtain the concentration of the target component in the sample.

If the amount of the bound magnetic particles at the detection surface 122 is lower than the predetermined threshold, the controller 15 continues to perform the following Steps 47 to 49.

In Step 47, the controller 15 further controls the first magnet 142 to generate the first magnet field so as to attract all of the magnetic particles to the detection surface 122.

Then, in Step 48, the controller 15 further controls the outflow valve 162 to be open to drain at least part of the sample out of the chamber 12, and then controls the outflow valve 162 to be closed and the inflow valve 162 to be open to allow the new sample to flow into the chamber 12.

Next, in Step 49, the controller 15 further controls the first magnet 142 to be switched off and the second magnet 144 to be switched on to generate the second magnetic field so as to pull the unbound magnetic particles away from the detection surface 122.

Then, the controller 15 continues to perform Steps 42 to 46.

In this embodiment, the number of sample replacements is determined based on the comparison of the measured amount of the bound magnetic particles and the predetermined threshold during the operation of the sensor device 10. Once the measured amount of the bound magnetic particles reaches the predetermined threshold, the sample replacement is ceased, which makes the detection of the sensor device 10 more flexible.

It should be noted that the above described embodiments are given for describing rather than limiting the invention, and it is to be understood that modifications and variations may be resorted to without departing from the spirit and scope of the invention as those skilled in the art readily understand. Such modifications and variations are considered to be within the scope of the invention and the appended claims. The protection scope of the invention is defined by the accompanying claims. In addition, any of the reference numerals in the claims should not be interpreted as a limitation to the claims. Use of the verb "comprise" and its conjugations does not exclude the presence of elements or steps other than those stated in a claim. The indefinite article "a" or "an" preceding an element or step does not exclude the presence of a plurality of such elements or steps.

What is claimed is:

1. A method of sampling, the method comprising the steps of:
   a. adding a sample to a chamber in which magnetic particles are provided, the sample including a target component and the chamber having a detection surface;
   b. exerting a magnetic force on the magnetic particles to attract the magnetic particles to the detection surface, wherein bound magnetic particles that capture the target component in the magnetic particles are held at the detection surface, and unbound magnetic particles that capture no target component in the magnetic particles are held at the detection surface as well;
   c. draining at least part of the sample out of the chamber and then adding a new sample to the chamber;
   d. altering the magnetic force exerted on the magnetic particles to release the unbound magnetic particles from the detection surface;
   e. repeating the steps b to d for a given number of cycles, wherein the step b further comprises, before the step of exerting, the step of:
   mixing the magnetic particles and the target component by generating an alternating magnetic field for a predetermined duration.

2. The method of a claim 1, further comprising the step of:
   measuring the amount of the bound magnetic particles that are held at the detection surface when the step of repeating is finished.
3. The method of claim 1, wherein the step of exerting comprises the step of:
   generating a first magnetic field to attract the magnetic particles to the detection surface;
   and the step of altering comprises the step of:
   ceasing to generate the first magnetic field so as to release the unbound magnetic particles from the detection surface; or
   ceasing to generate the first magnetic field and generating a second magnetic field so as to pull the unbound magnetic particles away from the detection surface.
4. The method of claim 3, wherein the second magnetic is a magnetic field that is opposite to the first magnetic field.
5. The method of claim 1, wherein the step d further comprises the step of:
   determining whether the amount of the bound magnetic particles that are held at the detection surface is above a predetermined threshold;
   if no, performing the steps b to d.
6. The method of claim 5, wherein the step of exerting comprises the step of:
   generating a first magnetic field to attract the magnetic particles to the detection surface;
   and the step of altering comprises the step of:
   ceasing to generate the first magnetic field so as to release the unbound magnetic particles from the detection surface; or
   ceasing to generate the first magnetic field and generating a second magnetic field so as to pull the unbound magnetic particles away from the detection surface.
7. A sensor device, comprising:
   a chamber in which magnetic particles are provided, the chamber having a detection surface and configured to receive a sample in which a target component is included;
   a magnetic manipulator configured to exert a magnetic force on the magnetic particles to attract the magnetic particles to the detection surface, wherein bound magnetic particles that capture the target component in the magnetic particles are held at the detection surface, and unbound magnetic particles that capture no target component in the magnetic particles are held at the detection surface as well; then to alter the magnetic force exerted on the magnetic particles to release the unbound magnetic particles from the detection surface;
   a sample replacing unit configured to replace at least part of the sample in the chamber with a new sample;
   a sensor unit configured to measure the amount of the bound magnetic particles that are held at the detection surface;
   a control unit coupled to the magnetic manipulator, the sample replacing unit and the sensor unit, wherein the control unit is configured to
   control the magnetic manipulator, the sample replacing unit, and the sensor unit to perform the method of claim 1.
8. A non-transitory computer-readable medium carrying computer code configured to control one or more computer processors to control a sensor device to perform the method of claim 1.
9. A method of sampling, the method comprising:
   i. adding a sample to a chamber in which magnetic particles are provided, the sample including a target component and the chamber including a detection surface;
   ii. after adding the sample, mixing the magnetic particles and the target component by generating an alternating magnetic field for a predetermined duration;
   iii. after the mixing, generating a first magnetic field to attract the magnetic particles to the detection surface such that bound magnetic particles that captured the target component and unbound magnetic particles that captured no target component are both held at the detection surface;
   iv. after attracting the magnetic particles to the detection surface, draining at least part of the sample out of the chamber and adding a new sample to the chamber;
   v. after adding the new sample to the chamber, releasing the unbound magnetic particles from the detection surface by one of ceasing to generate the first magnetic field or ceasing to generate the first magnetic field and generating a second magnetic field which pulls the unbound magnetic particles away from the detection surface;
   vi. repeating steps ii-v for a given plural number of cycles.
10. The method of claim 9, further including:
    after step vi, measuring an amount of the bound particles that are held at the detection surface.
11. A non-transitory computer-readable medium carrying software configured to control one or more computer processors to control a sensor device to perform the method according to claim 9, the sample device including the chamber, the first magnet, and the second magnet.
12. A sensor device comprising:
    a chamber including a detection surface and configured to receive magnetic particles and a sample including a target component which is captured in the magnetic particles to form bound magnetic particles, magnetic particles that capture no target component being unbound magnetic particles;
    a first magnet disposed adjacent the chamber and configured to attract bound and unbound magnetic particles to the detector surface;
    a second magnet disposed adjacent the chamber and configured to pull the unbound magnetic particles away from the detection surface;
    a sample replacing system configured to drain at least part of the sample out of the chamber and then add a new sample to the chamber;
    one or more control processors configured to control the first and second magnets and the sample replacing system to perform the method of claim 9.

* * * * *